US008929973B1

(12) United States Patent  
Webb et al.

(10) Patent No.: US 8,929,973 B1
(45) Date of Patent: Jan. 6, 2015

(54) APPARATUS AND METHOD FOR CHARACTERIZING OPTICAL SOURCES USED WITH HUMAN AND ANIMAL TISSUES

(75) Inventors: James S. Webb, Seattle, WA (US); Heather A. Ralph, Seattle, WA (US); Mark P. Bendett, Kirkland, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 1753 days.

(21) Appl. No.: 11/948,912

(22) Filed: Nov. 30, 2007

Related U.S. Application Data

(60) Provisional application No. 60/872,930, filed on Dec. 4, 2006.

(51) Int. Cl.
*A61B 6/00* (2006.01)
*A61B 5/00* (2006.01)

(52) U.S. Cl.
CPC .............. *A61B 5/0059* (2013.01); *A61B 5/0071* (2013.01); *A61B 5/0084* (2013.01)
USPC ........................................................ 600/476

(58) Field of Classification Search
CPC ... A61B 5/0059; A61B 5/0084; A61B 5/0071
USPC ........................................................ 600/476
See application file for complete search history.

(56) References Cited

U.S. PATENT DOCUMENTS

| 4,064,872 A | 12/1977 | Caplan |
| 4,215,694 A | 8/1980 | Isakov et al. |
| 4,232,678 A | 11/1980 | Skovajsa |
| 4,296,995 A | 10/1981 | Bickel |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |

(Continued)

FOREIGN PATENT DOCUMENTS

WO WO0025112 5/2000

OTHER PUBLICATIONS

Nakagawa A., et al., "Pulsed holmium:yttrium-aluminum-garnet laser-induced liquid jet as a novel dissection device in neuroendoscopic surgery", "J. Neurosurg.", Jul. 2004, pp. 145-150, vol. 101.

(Continued)

*Primary Examiner* — Tse Chen
*Assistant Examiner* — Hien Nguyen
(74) *Attorney, Agent, or Firm* — Charles A. Lemaire; Jonathan M. Rixen; Lemaire Patent Law Firm, P.L.L.C.

(57) ABSTRACT

Medical researchers use various optical devices for diagnosis, detection, treatment, and therapy. In some embodiments, they do not have the equipment necessary to determine how much light is emitted by the optical device or how far it penetrates tissue. The present invention provides for a method and apparatus for characterizing light from an optical device by using a tissue phantom. The method includes coupling light from an optical source into a device, transmitting the light through a tissue phantom, detecting a transmitted light, optionally electrically processing the detected output, and displaying the corresponding optical characterization. In some embodiments, the apparatus obtains input light from an optical source, and may include a tissue phantom, an optical detector, an electrical processing unit, and a display for displaying the corresponding optical characterization.

12 Claims, 3 Drawing Sheets

(56) References Cited

U.S. PATENT DOCUMENTS

| | | |
|---|---|---|
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,031,363 B2 | 4/2006 | Biard et al. |
| 7,040,805 B1 | 5/2006 | Ou et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,139,603 B2 | 11/2006 | Chance |
| 7,156,866 B1 | 1/2007 | Riggs et al. |
| 7,177,081 B2 | 2/2007 | Tomita et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,391,561 B2 | 6/2008 | Di Teodoro et al. |
| 7,402,167 B2 | 7/2008 | Nemenov |
| 7,647,112 B2 | 1/2010 | Tracey et al. |
| 7,654,750 B2 | 2/2010 | Brenner et al. |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,883,536 B1 | 2/2011 | Bendett et al. |
| 7,909,867 B2 | 3/2011 | Myung et al. |
| 7,951,181 B2 | 5/2011 | Mahadevan-Jansen et al. |
| 8,012,189 B1 | 9/2011 | Webb et al. |
| 2002/0002391 A1 | 1/2002 | Gerdes |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0156425 A1* | 8/2003 | Turnbull et al. ............. 362/545 |
| 2003/0236458 A1 | 12/2003 | Hochman |

(56) References Cited

U.S. PATENT DOCUMENTS

| | | | |
|---|---|---|---|
| 2004/0073101 A1 | 4/2004 | Chance | |
| 2004/0116985 A1 | 6/2004 | Black | |
| 2004/0176670 A1* | 9/2004 | Takamura et al. | 600/322 |
| 2004/0225339 A1 | 11/2004 | Yaroslaysky et al. | |
| 2004/0243111 A1 | 12/2004 | Bendett et al. | |
| 2004/0243112 A1 | 12/2004 | Bendett et al. | |
| 2005/0065531 A1 | 3/2005 | Cohen | |
| 2005/0096720 A1 | 5/2005 | Sharma et al. | |
| 2005/0099824 A1 | 5/2005 | Dowling et al. | |
| 2005/0142344 A1 | 6/2005 | Toepel | |
| 2005/0143789 A1 | 6/2005 | Whitehurst et al. | |
| 2005/0145786 A1* | 7/2005 | Rice et al. | 250/252.1 |
| 2005/0169597 A1 | 8/2005 | Colgan et al. | |
| 2005/0228256 A1 | 10/2005 | Labadie et al. | |
| 2005/0265586 A1* | 12/2005 | Rowe et al. | 382/124 |
| 2006/0095105 A1 | 5/2006 | Jog et al. | |
| 2006/0129210 A1 | 6/2006 | Cantin et al. | |
| 2006/0161218 A1 | 7/2006 | Danilov | |
| 2006/0161227 A1 | 7/2006 | Walsh et al. | |
| 2006/0276861 A1 | 12/2006 | Lin | |
| 2007/0053996 A1 | 3/2007 | Boyden et al. | |
| 2007/0054319 A1 | 3/2007 | Boyden et al. | |
| 2007/0060983 A1 | 3/2007 | Merfeld | |
| 2007/0060984 A1 | 3/2007 | Webb et al. | |
| 2007/0179557 A1 | 8/2007 | Maschino et al. | |
| 2007/0191906 A1 | 8/2007 | Iyer et al. | |
| 2007/0260297 A1 | 11/2007 | Chariff | |
| 2008/0077198 A1 | 3/2008 | Webb et al. | |
| 2008/0077200 A1 | 3/2008 | Bendett et al. | |
| 2009/0017096 A1* | 1/2009 | Lowman et al. | 424/426 |
| 2009/0076115 A1 | 3/2009 | Wharton et al. | |
| 2009/0163982 A1 | 6/2009 | DeCharms | |
| 2009/0177255 A1 | 7/2009 | Merfeld | |
| 2009/0210039 A1 | 8/2009 | Boyden et al. | |
| 2010/0049180 A1 | 2/2010 | Wells et al. | |
| 2010/0114190 A1 | 5/2010 | Bendett et al. | |
| 2010/0184818 A1 | 7/2010 | Wharton et al. | |
| 2010/0292758 A1 | 11/2010 | Lee et al. | |
| 2011/0172725 A1 | 7/2011 | Wells et al. | |

OTHER PUBLICATIONS

Passos D., et al., "Tissue phantom for optical diagnostics based on a suspension of microspheres with a fractal size distribution", "Journal of Biomedical Optics.", Nov.-Dec. 2005, pp. 064036, vol. 10, No. 6.
Allegre, et al., "Stimulation in the rat of a nerve fiber bundle by a short UV pulse from an excimer laser", "NeuroScience Letters", 1994, pp. 261-264, vol. 180.
Arridge et al., "The theoretical basis for the determination of optical pathlengths in tissue: temporal and frequency analysis", "Phys. Med. Biol.", 1992, pp. 1531-1560, vol. 37.
Chance et al., "Comparison of time-resolved and -unresolved measurements of deoxyhemoglobin in brain", "Proc. Nati. Acad. Sci. USA", Jul. 1988, pp. 4971-4975, vol. 85.
Fork, Richard L., "Laser Stimulation of Nerve Cells in Aplysia", "Science, New Series", Mar. 5, 1971, pp. 907-908, vol. 171, No. 3974.
Izzo, et al., "Laser Stimulation of the Auditory Nerve", "Lasers in Surgery and Medicine", 2006, Publisher: Wiley-Liss, Inc.
Izzo, et al., "Selectivity of neural stimulation in the auditory system: an comparison of optic and electric stimuli", "Journal of Biomedical Optics", Mar./Apr. 2007, pp. 021008, vol. 12, No. 2.
Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, p. 1108-1114, vol. 54, No. 6(1).
Maiorov, M., et al., "218 W quasi-CW operation of 1.83 um two-dimensional laser diode array", "Electronics Letters", Apr. 15, 1999, pp. 636-638, vol. 35, No. 8.
Princeton Lightwave, "High Power Multimode Laser Arrays", "www.princetonlightwave.com/content/pli_high_power_multimode_laser_arrays.pdf", 2005.
Princeton Lightwave, "High Power Water Cooled Laser Stack", "www.princetonlightwave.com", 2005.
Princeton Lightwave, "High Power Water Cooled Laser Stack", "http://www.princetonlightwave.com/content/pli_high_power_multimode_laser_stacks.pdf", 2005 (downloaded 12-.
Princeton Lightwave, "High Power Single Element Laser", "www.princetonlightwave.com/content/HP%20Single%20Element%20Laser%20version%202.pdf", 2005.
Rolfe, "In Vivo Near-Infrared Spectroscopy", "Annu. Rev. Biomed. Eng.", 2000, pp. 715-754, vol. 2.
Schwartz et al, "Auditory Brainstem Implants", "Neurotherapeutics: The Journal of the American Society for Experimental NeuroTherapeutics", Jan. 2008, pp. 128-136, vol. 5.
Teudt, et al., "Optical Stimulation of the Facial Nerve: A New Monitoring Technique?", "The Laryngoscope", 2007, pp. 1641-1647, vol. 117, No. 9.
Wells, Jonathon, et al., "Application of Infrared Light for in vivo Neural Stimulation.", "Journal of Biomedical Optics", Nov. 2005, pp. 064003-1 to 064003-12, vol. 10, No. 6.
Augustine, George J., "Combining patch-clamp and optical methods in brain slices", "Journal of Neuroscience Methods", 1994, pp. 163-169, vol. 54.
Banghart, Matthew, et al., "Light-activated ion channels for remote control of neuronal firing", "Nature Neuroscience", Nov. 21, 2004, pp. 1381-1386, vol. 7, No. 12.
Boyden, Edward S., et al., "Millisecond-timescale, genetically targeted optical control of neural activity", "Nature Neuroscience", Sep. 2005, pp. 1263-1268, vol. 8, No. 9.
Bureau, Ingrid, et al., "Precise Development of Functional and Anatomical Columns in the Neocortex", "Neuron", Jun. 10, 2004, pp. 789-801, vol. 42.
Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.
Deal, Walter J., et al., "Photoregulation of Biol. Activity by Photochromic Reagents, 3. Photoreg. of Bioelectricity by Acetylcholine Receptor Inh", "Proc. Natl. Acad. Sci.", 1969, pp. 1230-1234, vol. 64, No. 4.
Dodt, H.-U., et al., "Circuitry of rat barrel cortex investigated by infrared-guided laser stimulation", "NeuroReport", Mar. 24, 2003, pp. 623-627, vol. 14, No. 4.
Dodt, H.-U., et al., "Precisely Localized LTD in the Neocortex Revealed by Infrared-Guided Laser Stimulation.", "Science", Oct. 1, 1999, pp. 110-113, vol. 286.
Eder, Matthias, et al., "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.
Han, Xue, et al., "Multiple-Color Optical Activation, Silencing, and Desynchronization of Neural Activity, with Single-Spike Temporal Resol", "PLoS ONE 2(3): e299. doi:10.1371/journal.pone.0000299", Mar. 2007, pp. e299, No. 3, Publisher: www.plosone.org.
Naples, et al., "A spiral nerve cuff electrode for peripheral nerve stimulation", "IEEE Trans Biomed Eng", Nov. 1988, pp. 905-916, vol. 35, No. 11.
Vogel, Alfred, et al., "Mechanisms of pulsed laser ablation of biological tissues.", "Chemical Reviews", 2003, pp. 577-644, vol. 103, No. 2.
Wells, Jonathon, et al., "Optical stimulation of neural tissue in vivo", "Optics Letters", Mar. 1, 2005, pp. 504-506, vol. 30, No. 5.
Wells, Jonathon D., et al., "Optically Mediated Nerve Stimulation: Identification of Injury Thresholds.", "Lasers in Surgery and Medicine ", Jul. 23, 2007, pp. 513-526, vol. 39.
Wells, Jonathon, et al., "Pulsed laser versus electrical energy for peripheral nerve stimulation", "Journal of Neuroscience Methods", 2007, pp. 326-337, vol. 163.
Yoo, et al., "Selective recording of the canine hypoglossal nerve using a multicontact flat interface nerve electrode", "IEEE Trans Biomed Eng", Aug. 2005, pp. 1461-1469, vol. 52, No. 8.
Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.
Zhang, Feng, et al., "Channelrhodopsin-2 and optical control of excitable cells", "Nature Methods", Sep. 21, 2006, pp. 785-792, vol. 3, No. 10.

* cited by examiner

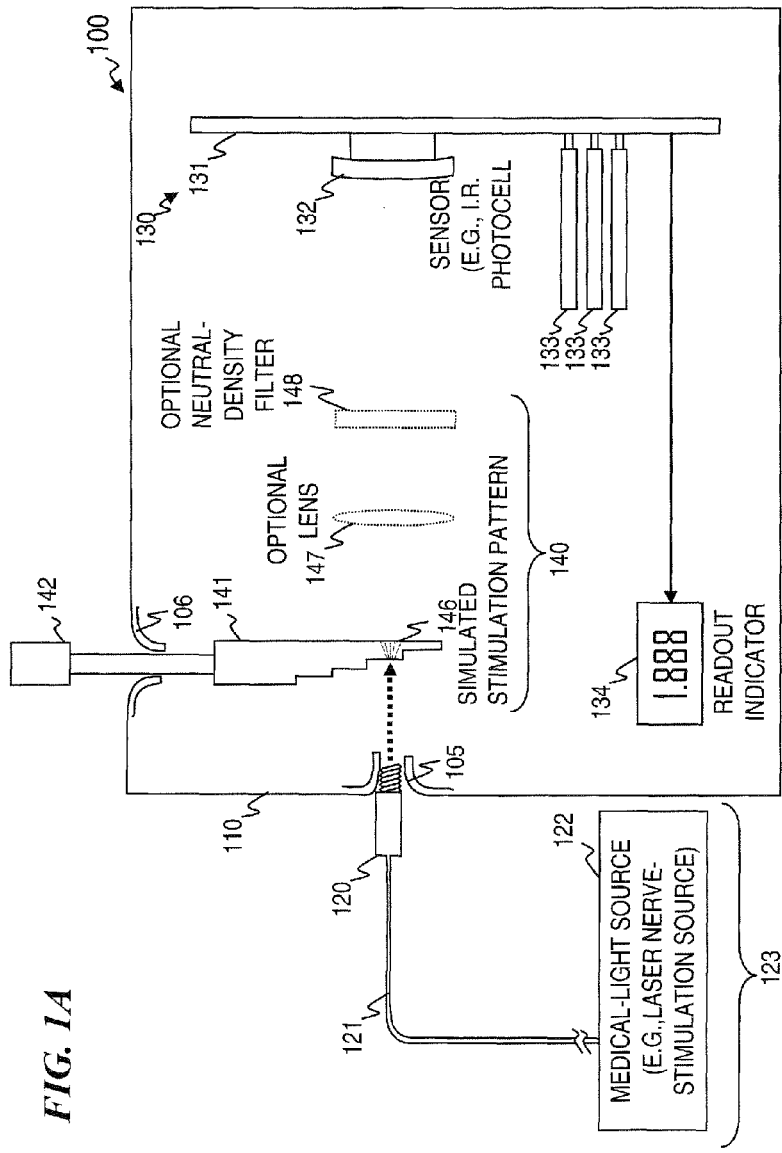

APPARATUS AND METHOD FOR CHARACTERIZING OPTICAL SOURCES USED WITH HUMAN AND ANIMAL TISSUES

CROSS-REFERENCE TO RELATED APPLICATIONS

This invention claims benefit of U.S. Provisional Patent Application Ser. No. 60/872,930 filed Dec. 4, 2006 by James S. Webb et al. and entitled "APPARATUS AND METHOD FOR CHARACTERIZING OPTICAL SOURCES USED WITH HUMAN AND ANIMAL TISSUES," which is hereby incorporated by reference in its entirety. This invention is also related to U.S. Provisional Patent Application Ser. No. 60/715,884 filed September 9, 2005 by James S. Webb et al. and entitled "APPARATUS AND METHOD FOR OPTICAL STIMULATION OF NERVES," U.S. patent application Ser. No. 11/257,793 filed Oct. 24, 2005 by James S. Webb et al. and entitled "APPARATUS AND METHOD FOR OPTICAL STIMULATION OF NERVES AND OTHER ANIMAL TISSUE" (which issued as U.S. Pat. No. 7,736,382 on Jun. 15, 2010), U.S. patent application Ser. No. 11/536,639 filed Sep. 28, 2006 by James S. Webb et al. and entitled "MINIATURE APPARATUS AND METHOD FOR OPTICAL STIMULATION OF NERVES AND OTHER ANIMAL TISSUE" (which issued as U.S. Pat. No. 7,988,688 on Aug. 2, 2011), and U.S. patent application Ser. No. 11/536,642 filed Sep. 28, 2006 by Mark P. Bendett et al. and entitled "APPARATUS AND METHOD FOR STIMULATION OF NERVES AND AUTOMATED CONTROL OF SURGICAL INSTRUMENTS" (which published as U.S. Patent Application Publication 2008/0077200 on Mar. 27, 2008), which are all incorporated herein in their entirety by reference.

FIELD OF THE INVENTION

The invention relates generally to tissue optics (interactions of light with human or animal tissue), and more particularly to methods and apparatus to characterize optical sources (sources of light energy at various wavelengths) used in medical treatments and research involving light such as infrared or optical nerve stimulation, laser-vision correction, cosmetic laser skin treatments like laser hair removal, photodynamic therapy, and microdisection and microablation.

BACKGROUND OF THE INVENTION

Medical professionals use various optical devices for research, diagnosis, detection, treatment, and therapy. Such optical devices generate, condition, and/or deliver light that may be used to optically stimulate nerves or correct eyesight, for example. Typically, medical researchers do not have the measurement devices necessary to determine how far the light penetrates into a tissue or what cross-sectional area is illuminated. To determine these quantities, the researcher needs to measure power, beam diameter and shape, divergence, and wavelength, as well as the optical properties of the tissue in question.

U.S. Pat. No. 6,475,800 issued to Hazen, et al. on Nov. 5, 2002 entitled "Intra-serum and intra-gel for modeling human skin tissue" and is hereby incorporated by reference. Hazen et al. describe a class of samples that model the human body and are based upon emulsions of oil in water with lecithin acting as the emulsifier. These solutions that have varying particle sizes may be spiked with components (albumin, urea and glucose) to simulate skin tissues, and used in the medical field where lasers and spectroscopy-based analyzers are used in treatment of the body. Hazen et al. say that the samples allow one to gather data on net analyte signal, photon depth of penetration, photon radial diffusion, photon interaction between tissue layers, photon density (all as a function of frequency) and on instrumentation requirements such as resolution and dynamic range.

U.S. Pat. No. 6,224,969 issued to Steenbergen, et al. on May 1, 2001 entitled "Optical phantom suitable for stimulating the optical properties of biological material and a method of producing said phantom" and is hereby incorporated by reference. Steenbergen, et al. describe an optical phantom for simulating optical properties of biological material and a method of making the phantom, which includes a matrix of poly(vinyl alcohol) (PVA) and spherical particles whose refractive index differs from that of the PVA. Preferably the PVA has a level of hydrolysis of >98%, and the spherical particles are hollow polystyrene particles. In addition, light-absorbing and light-scattering substances may be added.

U.S. Pat. No. 6,353,226 issued Mar. 5, 2002 and U.S. Pat. No. 6,630,673 issued Oct. 7, 2003 to Khalil et al., both titled "Non-invasive sensor capable of determining optical parameters in a sample having multiple layers," and are hereby incorporated by reference. The apparatus measures light that is substantially reflected, scattered, absorbed, or emitted from a shallower layer of the sample of tissue, measures light that is substantially reflected, scattered, absorbed, or emitted from a deeper layer of the sample of tissue, determines at least one optical parameter for each of these layers, and accounts for the effect of the shallower layer on the at least one optical parameter of the deeper layer.

U.S. Pat. No. 5,261,822 to Hall, et al. issued Nov. 16, 1993 entitled "Surgical refractive laser calibration device", and U.S. Pat. No. 5,464,960 issued to Hall, et al. on Nov. 7, 1995 entitled "Laser Calibration Device" which are both hereby incorporated by reference, each describe a phantom cornea for calibrating surgical lasers is formed by superimposition of thin-films of alternating colors. After ablation by a laser beam, the resulting spherical cavity appears as a pattern of nested circles whose concentricity and spacing reflect the alignment and intensity of the laser beam.

U.S. Patent Publication US 2005/0142344 by Michael Toepel entitled "Laser Test Card" is hereby incorporated by reference. Toepel describes a card for testing and displaying a shape of a laser beam.

U.S. Pat. No. 5,480,482 that issued to Novinson on Jan. 2, 1996 entitled "Reversible thermochromic pigments", is incorporated herein by reference, and describes a color changing pigment composition which changes color reversibly when ted comprising (a) a cyclic aryl lactone dye, (b) a diaminoalkane activator and (c) an ester. The pigment composition can also include a white pigment such as titanium dioxide as an opacifier or a yellow dye such Hansa yellow G. The pigment composition changes from a dark color, e.g., blue, to white when the composition is heated to a specified temperature, e.g., to a temperature of 52 degrees C., and reversibly changes from white back to the blue color when the pigment composition is cooled, e.g., to a temperature below about 25 degrees C.

U.S. Pat. No. 6,669,765 that issued to Senga, et al. on Dec. 30, 2003 entitled "Thermochromic dry offset ink, and printed article produced using the same", is incorporated herein by reference, and describes a thermochromic dry offset ink comprising a dry offset ink medium and a thermochromic pigment material dispersed therein, wherein the thermochromic pigment material is a pigment material which has a microcapsular form having non-round particle cross section and has a thermochromic material enclosed in the microcapsules. Also disclosed is a printed article produced using the ink. The thermochromic dry offset ink can more improve pressure resistance and heat resistance and also can more satisfy uniform printability and high-speed continuous printability in offset printing especially on articles such as containers.

U.S. Pat. No. 4,681,791 that issued to Shibahashi, et al. on Jul. 21, 1987 titled "Thermochromic textile material", is incorporated herein by reference, and describes a textile material in the form of fiber, raw stock, yarn or fabric, which comprises fibers each of which is coated with a thermochromic layer containing a thermochromic pigment having a particle size satisfying [a particular formula] of a fiber. The textile material can undergo reversible color change in a wide variety of colors and can be applied to any kind of textile products.

U.S. Pat. No. 6,444,313 that issued to Ono, et al. on Sep. 3, 2002 entitled "Thermochromic acrylic synthetic fiber, its processed article, and process for producing thermochromic acrylic synthetic fiber", is incorporated herein by reference, and describes a thermochromic acrylic synthetic fiber comprising an acrylonitrile polymer in which a thermochromic pigment composition with an average particle diameter of from 0.5 micron to 30 microns is dispersedly contained in an amount of from 0.5% by weight to 40% by weight based on the weight of the polymer, and being made into fibers; the pigment composition containing (a) an electron-donating color-developing organic compound, (b) an electron-accepting compound and (c) a reaction medium that determines the temperature at which the color-developing reaction of the both compounds takes place. Also disclosed are a processed article of the above thermochromic acrylic synthetic fiber, and a process for producing the thermochromic acrylic synthetic fiber.

U.S. Pat. No. 7,040,805 that issued to Ou, et al. on May 9, 2006 titled "Method of infrared thermography", is incorporated herein by reference, and describes "A method of infrared thermography is described. The invention utilizes a high resolution infrared thermography system with an infrared camera and associated computer in conjunction with a test chamber to determine heat-transfer coefficients and film effectiveness values from a single test.

U.S. Pat. No. 6,585,411 that issued to Hammarth, et al. on Jul. 1, 2003 titled "Aerosol dispenser temperature indicator", is incorporated herein by reference, and describes a liquid crystal temperature indicator, and aerosol dispensers equipped with a properly placed indicator, to facilitate using aerosols within preferred temperature ranges or at optimum temperatures. The temperature indicator uses different colors to graphically illustrate temperatures and/or temperature ranges, as well as temperatures above and below optimal temperatures or preferred temperature ranges. Temperature indicators are reusable; they may be self-adhesive and may optionally be transferred from a liquid crystal temperature indicator is either permanently or reversibly adhered to the outer surface of an aerosol dispenser in a location that will allow estimation of the temperature of the liquid inside the dispenser. Liquid crystals are composed of elongated organic molecules that can exhibit different physical properties (e.g., optical and electrical properties) at different temperatures. Using, for example, changes in the color of a plurality of liquid crystals at different temperatures arranged in numerical (i.e., ascending or descending) order, temperature indicators of the present invention can be coupled to aerosol dispensers to indicate desired temperature adjustments to a dispenser within a range of temperatures. The temperature indicators thus act as guides for the use of appropriate heat flow control methods for achieving preferred temperature conditions for making and using aerosol. United States Patents related to temperature measurement using liquid crystals include U.S. Pat. No. 4,064,872 (Caplan), issued Dec. 27, 1977; U.S. Pat. No. 6,257,759 (Witonsky, et al.), issued Jul. 10, 2001; U.S. Pat. No. 6,294,109 (Ratna, et al.); and U.S. Pat. No. 6,284,078 (Witonsky, et al.), issued Sep. 4, 2001, each of which is incorporated herein by reference.

In an article by Passos D. et al., "Tissue phantom for optical diagnostics based on a suspension of microspheres with a fractal size distribution," J Biomed Opt. 2005 November-December; 10(6):064036 (which is hereby incorporated by reference) there is a description of a phantom for reproducing the phase function, absorption, and scattering coefficients of a real biological tissue (adult brain white matter and liver) using a suspension of polystyrene microspheres with a fractal size distribution. The design of a light scattering goniometer with a cylindrical cell in air is discussed, and phase function measurements using the device are described.

The paper by Viator J A, et al., "Spectra from 2.5-15 microns (i.e., micrometers) of tissue phantom materials, optical clearing agents and ex vivo human skin: implications for depth profiling of human skin," Phys Med Biol. 2003 Jan. 21; 48(2):N15-24 (which is hereby incorporated by reference) describes tissue phantoms for human skin in the IR wavelengths; it also details the constituents used for the phantom and their relation to the optical properties. They used Fourier-transform infrared spectroscopy in attenuated total reflection mode to measure the infrared absorption spectra, in the range of 2-15 microns, of water, polyacrylamide, Intralipid, collagen gels, four hyperosmotic clearing agents (glycerol, 1,3-butylene glycol, trimethylolpropane, Topicare), and ex vivo human stratum corneum and dermis.

Papers by Nakagawa A., et al., "Pulsed holmium:yttrium-aluminum-garnet laser-induced liquid jet as a novel dissection device in neuroendoscopic surgery." J. Neurosurg. 2004 July; 101(1):145-50 and Nakagawa A., et al., "Holmium: YAG laser-induced liquid jet knife: possible novel method for dissection." Lasers Surg Med. 2002; 31(2):129-35 (which are hereby incorporated by reference) describe use of the Ho:YAG in neuroendoscopic ablative surgery applications for small-vessel ablation. This would be useful for muscle tissue phantoms, since blood vessels are made up of smooth muscle. The authors of the first paper describe experiments aimed at solving problems associated with pressure-driven continuous jet of water for neuroendoscopic dissection by using a pulsed holmium:yttrium-aluminum-garnet (Ho: YAG) laser-induced liquid jet (LILJ). They examined its mechanical characteristics and controllability in an artificial tissue phantom (10% gelatin of 1-mm thickness). The authors of the first paper describe the effect on artificial organs made of 10 and 30% (w/v) gelatin, each of which represent features of soft tissue and blood vessels.

The paper by Ovelmen-Levitt J., et al., "Brain ablation in the rat cerebral cortex using a tunable-free electron laser," Lasers Surg Med. 2003; 33(2):81-92 (which is hereby incorporated by reference) describes research done at Vanderbilt using their MARK III free electron laser (FEL) tuned to molecular vibrational absorbance maxima in the infrared (IR) wavelength range of 3.0-6.45 microns to study the effect of these various wavelengths and a power level of 5 mJ/2 microseconds macropulse on photoablation of CNS (central-nervous-system) tissue.

There are relatively high costs and various difficulties encountered using the above methods and apparatus. Accordingly, there is a need for an apparatus and method that, in a standardized manner, can cheaply, easily, and directly characterize the optical sources used in optical devices and their interactions with different types of tissue.

BRIEF SUMMARY OF THE INVENTION

In some embodiments of the present invention, a method is described that includes providing light from an optical source, shining the output beam onto a "tissue phantom," allowing the light to be transmitted, scattered, absorbed, and potentially reemitted, detecting the transmitted light on the far side of the tissue phantom, optionally processing the detector response, and displaying the result, either visibly as an image or with a numeric readout that corresponds to an optical characterization associated with the light.

In some embodiments of the present invention, an apparatus is described that includes light from an optical source, a tissue phantom, a detector, an optional electrical or nonelectrical processing unit, and a display for displaying a numeric result and/or graphical image that corresponds to an optical characterization associated with the light.

In some embodiments, the present invention includes an apparatus comprising means for inputting light from an optical source, means for simulating an organic tissue, means for transmitting, scattering, absorbing, and potentially reemitting the light in a simulated organic tissue, means for detecting the transmitted light, optional means for electrically processing the light on the output side of the "tissue phantom," and means for displaying a numeric result and/or graphical image that corresponds to an optical characterization associated with the light.

BRIEF DESCRIPTION OF THE DRAWINGS

FIG. 1A is a schematic of a tissue-penetration-depth monitor (TPDM) 100.

FIG. 1B is a schematic of a rectangular-shaped tissue phantom 149.

FIG. 1C is a schematic of a wedge-shaped tissue phantom 150.

FIG. 1D is a schematic of a tissue phantom 151 that has steps of different thicknesses.

DETAILED DESCRIPTION OF THE INVENTION

Figure 3:
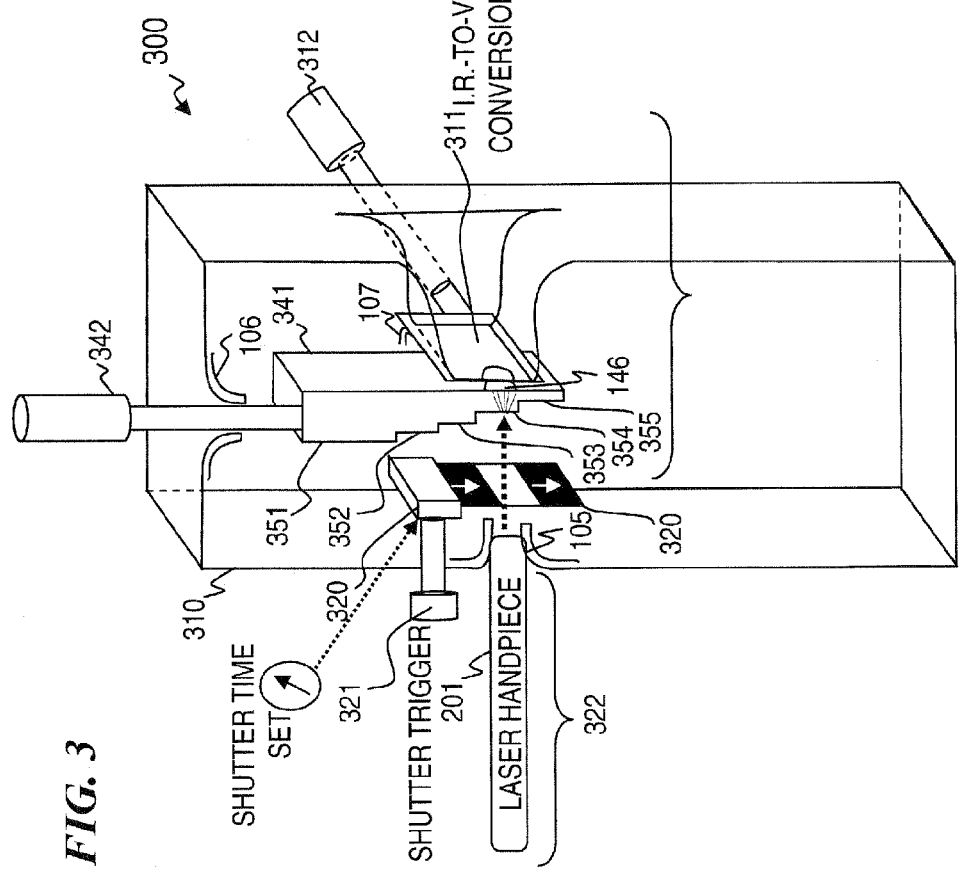
FIG. 3 is a schematic of a TPDM 300 that can display the IR output from a laser handpiece 201 as visible light.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component that appears in multiple Figures. Signals and connections may be referred to by the same reference number or label, and the actual meaning will be clear from its use in the context of the description.

FIG. 1A is a schematic of a tissue-penetration-depth monitor (TPDM) 100. The TPDM 100 is used to characterize the optical source (e.g., optical power, beam diameter, and divergence) and its interaction with a specified tissue (e.g., transmitted power, dispersion, scatter, and absorption) of a medical light source (MLS) 122. (The TPDM 100 can be used with any medical light source 122 (e.g., photo-dynamic-therapy lasers, dental lasers and light sources, eye-surgery lasers, low-light-level-therapy optical sources, cosmetic laser treatment sources such as hair or tattoo removal lasers, nerve-stimulation optical sources (such as lasers, light-emitting diodes (LEDs) or other optical sources capable of optically stimulating nerves in an animal), and the like). In some embodiments, for example, the TPDM 100 can determine tissue-penetration depth, provide a calibrated measurement of transmitted power, provide spot size and beam-profile measurements, or provide absorbed power measurements. In some embodiments, the TPDM has an overall enclosure 110 that includes an input fiber connector 120 (e.g. an SMA-type fiber connector, an FC-type fiber connector, or a v-groove to place a fiber probe against.) In some embodiments, the output of the MLS 122 (e.g., infrared light (IR light), visible light, pulsed laser light, ultraviolet (UV) laser light, broadband LED output, superluminescent or other narrowband LED output, continuous wave (CW) laser light, or tunable laser light) is coupled into the TPDM 100 via a fiber or fiber probe 121 which inserts into aperture 105 of TPDM 100 at input fiber connector 120.

Upon entering the TPDM 100, the light from the MLS 122 passes through a tissue phantom 141 that has substantially the same optical properties as a particular tissue type (e.g. skin, neurons, fat, muscle), an optional lens 147 that forms an image, and an optional neutral density filter (NDF) 148 that reduces the intensity of the light before it is detected. Light from MLS 122 travels into the closer side of the tissue phantom, is acted upon (e.g. transmitted, absorbed, scattered, and refracted) by the tissue phantom and a transmitted beam 146 is formed on the far surface of tissue phantom 141 (the right-hand surface in FIG. 1A), and this transmitted beam 146 can then be processed by the optional lens 147 and the optional NDF 148. The transmitted beam 146 approximates the beam that would be generated (e.g., by transmission, scattering, absorption, fluorescence, and/or other interactions) if the light from the MLS 122 was passed through actual human and/or animal tissue of a given depth and tissue composition. In some embodiments, the tissue phantom 141, which is formed of materials that have substantially the same optical properties at the relevant wavelengths as one or more types of human tissue, is connected to a handle 142 so that it can be inserted and removed from the TPDM 100. In some embodiments, tissue phantom 141 is inserted in the TPDM 100 at a phantom insertion port 106. In some embodiments, the phantom insertion port 106 includes a seal also made of flexible opaque rubber, forms a light-tight seal around the issue phantom 141, and, when the tissue phantom 141 is removed, automatically closes to prevent laser light from fiber 121 from exiting through phantom insertion port 106 and to prevent outside light from entering the TPDM 100 (this is useful when using TPDM 100 to image the end of LNSS 122 without a tissue phantom, e.g., to verify that its tip is clean and unobstructed). In some embodiments, the phantom can be inserted a measured distance (e.g. as measured by rulings on the tissue phantom). For tissue phantoms with variable thicknesses, inserting the phantom further would simulate a thicker tissue sample (in some embodiments).

In some embodiments, the light that transmits through the tissue phantom 141 must be processed for presentation to a human user. Many different detectors are possible. FIG. 1A and FIG. 2 show embodiments that use electronic processing of the light that passes through the tissue phantom, while FIG. 3 shows and embodiment that uses non-electronic processing of the infrared (IR) signal to a form visible to a human.

In FIG. 1A, the transmitted light next undergoes electrical processing 130 for presentation of an analysis or representation of the light to a human user. The transmitted light is detected by electrical detector 132, which is connected to a motherboard 131. In some embodiments, the detector 132 is a thermopile power meter used to measure actual transmitted power. In some embodiments, the detector 132 is an infrared photocell. In some embodiments, the detector 132 is a linear or two-dimensional charge-coupled device (CCD) camera array.

In some embodiments, one or more processing units 133, which are also connected to the motherboard 131, convert the input from the detector 132 into a signal that is sent to a display 134. In some embodiments, display 134 is on the outside of the TPDM 100. In some embodiments display 134 displays a numeric readout of the optical power or optical power density at a given tissue-penetration depth that corresponds to the current thickness of the tissue phantom (or other optical characterization) that is associated with the MLS 122. In other embodiments, display 134 also or alternatively displays one or more dimensions of the transmitted light (e.g., the full-width half-maximum (FWHM) measurement of the transmitted beam diameter in one or more directions (e.g., either in the X direction, the Y direction, or both, or using one or more other suitable measurements such as angle or area). In some embodiments, display 134 also or alternatively displays a pulse frequency, pulse duration, pulse repetition rate, pulse period, duty cycle and/or other data characterizing the light's temporal operation if the light is pulsed. In some embodiments, the display 134 shows a profile of the optical power density as a function of position on the detector, producing a beam profile.

In some embodiments, the incident side of the TPDM 100 has various methods for positioning the optical input to the TPDM 100. In some embodiments, for example, the TPDM 100 has a V-groove in the surface that allows the user to set the optical input against the TPDM without damaging the tip. In some embodiments, the distance to the actual tissue phantom is calculated based on the diameter of the probe and the angle of the V-groove. In another embodiment, for example, the TPDM 100 has a surface along which a user can slide their optical input, to traverse along the tissue phantom 141.

Figure 1E:
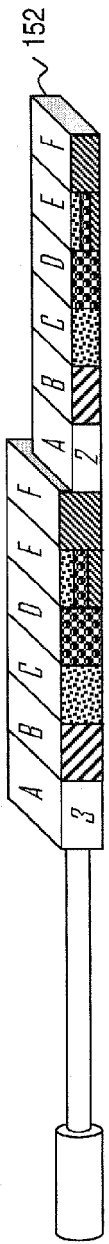
FIG. 1E is a schematic of a tissue phantom 152 that has steps of different thicknesses.
Figure 2:
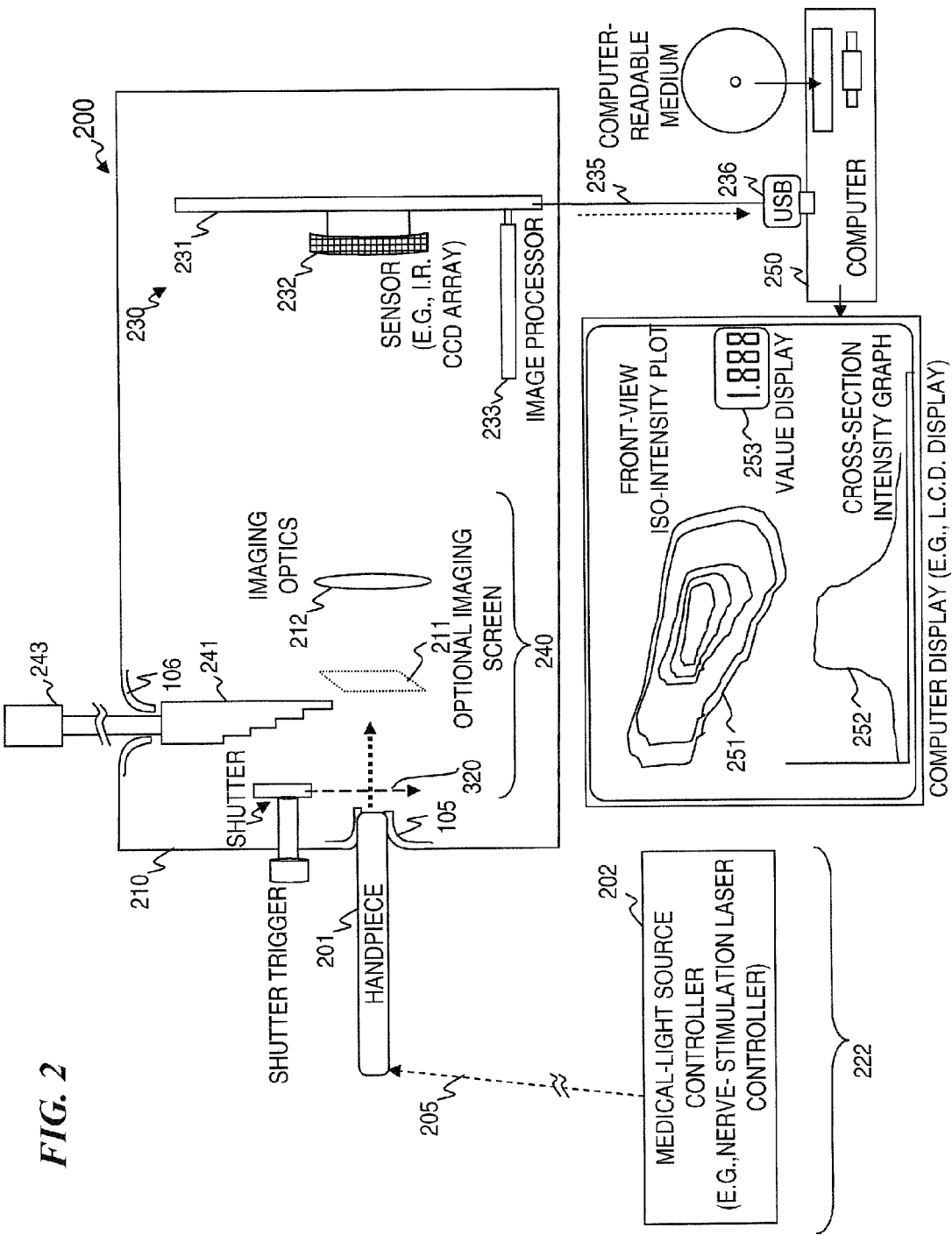
FIG. 2 is a schematic of a TPDM 200 used to characterize the optics of a laser handpiece 201.

FIGS. 1B through 1D are schematics of various designs for the tissue phantom 141. FIG. 1B is a tissue phantom 149 that is rectangular in shape with one uniform depth. In some embodiments, tissue phantom 149 is of a single homogeneous material, while in other embodiments, a plurality of layers of different materials are used to simulate multiple layers of organic tissue (e.g., skin, muscle, fat and/or bone). In some embodiments, as described for FIG. 1E, phantom 149 uses one thickness, but has a plurality of different materials are placed side-by-side in a single tissue-phantom device such that different tissues can be quickly analyzed by moving one or another of the different areas of one or more layers of different materials (e.g., side-by-side areas having skin only in one area, skin and muscle in another area, skin and fat in another area, skin muscle and bone in another area, muscle and bone in another area, and/or other combinations). FIG. 1C is a tissue phantom 150 that is wedge-shaped with the depth varying from a thicker thickness at the handle end to a thinner thickness at the end opposite the handle end. FIG. 1D shows a tissue phantom 151 that has steps of varying thicknesses. In FIG. 1E (see drawing sheet with FIG. 3), a plurality of different materials are placed side-by-side in a single tissue-phantom device, but including a plurality of different thicknesses for at least some of the tissue types as well, such that different tissues can be quickly analyzed by moving one or another of the different areas of one or more layers of different materials (e.g., side-by-side areas having skin only in one area, skin and muscle in another area, skin and fat in another area, skin muscle and bone in another area, muscle and bone in another area, and/or other combinations). In some embodiments, the tissue phantom 141 is made of a gel or liquid sandwiched between two glass or plastic plates. The glass or plastic material (e.g. fused silica, sapphire crystal, or polycarbonate) is selected to transmit highly over a large range of wavelengths. Several different tissue types might be mimicked by the tissue phantom 141 using different materials. The tissue phantom 141 may simulate multiple layers of different kinds of tissues by including different layers of materials. In addition or alternatively, in some embodiments, different tissues are mimicked in the same tissue phantom. In addition or alternatively, in some embodiments, different tissues are mimicked in different versions of the tissue phantom. In some embodiments, a plurality of tissue phantoms 141 can be inserted simultaneously into TPDM 100 (FIG. 1A), TPDM 200 (FIG. 2) or TPDM 300 (FIG. 3) to simulate multiple layers of different kinds of tissue.

FIG. 2 is a schematic of a TPDM 200 used to characterize the output from laser handpiece 201. In some embodiments, the output from the laser handpiece 201 is controlled by an exposure controller 202 (e.g., optionally including a manual shutter 320, or electrical shutter or foot control within controller 202 through control link 205), that, in some embodiments, is located remotely (e.g., on the floor or in a neighboring room). The light emitted from the handpiece 201 (e.g., IR light) can either pass through a tissue phantom 242, connected to a handle 243, or the tissue phantom 242 can be removed and the light can pass straight through to the optional imaging optics and detector. In some embodiments, if the light from the laser handpiece 201 passes straight through because there is not tissue phantom 241 in the beam path (e.g., the imaging optics 212 are focused to the tip of the handpiece 201 such that the system obtains an image of the endface of the handpiece 201), the TPDM 200 can be used to determine if the end face 201 of the output of the medical light source (MLS) 222 is clean or not. In other embodiments, the imaging optics 212 are focused to some intermediate focal plane (e.g., in some embodiments, optionally using a translucent object screen 211). For example, if the end face is dirty, the beam incident on the detector 232 will not be uniform or symmetric, so the image 251 generated by the TPDM 200 will not be uniform or symmetric. After the light from the laser handpiece 201 passes through optional tissue phantom 242, the light goes through the optional imaging optics 212. In some embodiments, for example, the imaging optics 212 includes a lens that reimages the light onto the detector 232 so that it can undergo electrical processing 230. In some embodiments, housing 210 includes a light-tight box that encloses at least the end of laser handpiece 201, the tissue phantom 242, any screen 211 and/or focusing optics 212, and detector 232.

A detector 232 contains various grids of pixels and is connected to a motherboard 231. Image processor 233, which is also connected to the motherboard 231, converts the input from the detector 232 into data that is sent to the exterior of the TPDM 200 via a data line 235. On the exterior of the TPDM 200, the data line 235 continues out until it ends at an optional Universal Serial Bus (USB) connector 236. The optional USB connector 236 or the data line 235 is plugged into a processor (e.g., a personal computer) 250. The processor 250 takes the data from the data line 235 and converts it into various images and numeric readouts that represent the input to the detector 232. These images and readouts are displayed by a display 260 (e.g., a liquid-crystal-display (LCD) monitor). In some embodiments, the processor 250 creates a display image 251 of the transmitted light incident on the detector 232. The display image 251 can show the intensity profile of the transmitted light incident on the detector 232, the intensity profile of the light at the laser handpiece 201, and/or, as mentioned above, it can be used to determine whether the end face of the laser handpiece 201 is dirty. In some embodiments, the processor 250 also creates a graph 252 representing the cross-sectional intensity of the light incident on the detector 232. In some embodiments, the processor 250 creates a numeric readout 253 which represents the tissue penetration depth (or other optical characterization) that is associated with the output of the MLS 222.

FIG. 3 shows a non-electronic processing system 300 wherein, in some embodiments, the detector 311 is a card made of material coated with fluorescing chromophores. Some embodiments of system 300 optionally include an automatic opening and closing aperture 105, which opens when laser handpiece 201 is thrust into it, and which automatically closes when laser handpiece 201 is withdrawn. Similarly, in some embodiments, an automatic opening and closing aperture 106 is provided for insertion and position adjusting of tissue phantom 341, as controlled by handle 342, and/or an automatic opening and closing aperture 107 is provided for insertion and position adjusting of detector card 311 on handle 312. In some embodiments, different chromophores would be used for different wavelengths of light or different intensities of light. The detectors 311 could be swapped for use with different medical light source (MLS) 322 or tissue phantoms 341. In some embodiments, detector 311 is a ceramic wafer having a non-linear material that doubles or triples the frequency of the IR stimulation radiation from MLS 322 (e.g., 1060-nm IR radiation would be frequency doubled to 530-nm blue-green light, 1300-nm IR radiation would be frequency doubled to 650-nm red light, 1550-nm IR radiation is frequency tripled to 517-nm blue-green light and/or 1800-nm IR radiation is frequency tripled to 600-nm orange-red light). In some embodiments, the present invention uses (for detector 311, which is permanently or removably installed) a standard color-change ceramic wafer having a non-linear up-conversion material, such as VIEW-IT® discs available from www.kentek.com (Kentek Corporation, 1 μm St., Pittsfield, N.H. 03263, United States). In some embodiments, a shutter 320 having a time-adjustment mechanism 322 and/or shutter trigger 321, in order to limit the time that detector 311 is exposed to output of the MLS 322, as modified by the tissue phantom 341, and thus provide a more accurate indication of the power and/or energy of the stimulation laser beam.

In other embodiments, detector 311 is a permanent-change multilayer card wherein, when exposed to light of sufficient energy one or more successive layers are ablated away or change color in order to show the pattern and intensity of the laser beam. For example, in some embodiments, the outermost interacting layer is black and is removed or changes color when exposed to the lowest-energy interacting beam. Deeper layers would require higher intensity light to ablate or change color (e.g., for very low intensity beams that still have enough energy, the outermost layer(s) ablates or otherwise changes to expose one or more lower-level layers that have different colors and energy-absorption characteristics). In some embodiments, the present invention uses, for detector 311, a card such as described in U.S. patent application Ser. No. 10/744,127 (Patent Publication US 2005/0142344) by Michael Toepel entitled "Laser Test Card" which is hereby incorporated by reference. In some embodiments, the present invention uses (for detector 311) a standard color-change test paper, such as ZAP-IT® available from www.zap-it.com or www.kentek.com (Kentek Corporation, 1 μm St., Pittsfield, N.H. 03263, United States), wherein a plurality of different color changes each correspond to a particular power or energy in the output of the MLS 122. In some such embodiments, the tissue phantom is modified and calibrated such that a particular color on the test paper will correspond to a particular irradiance of transmitted light (e.g., level of nerve stimulation and/or a level of tissue damage from the optical source). For example, if a standard tissue phantom (i.e., one that accurately simulated the reduction in intensity and the dispersion that light would undergo traveling through a given tissue of a given thickness) would affect (e.g., ablate) too many layers of detector 311, the modified tissue phantom 341 in system 300 would be darkened and/or thickened (thus reducing the transmitted power and energy) in order that the desired range of stimulation intensities would activate the available range of colors on the permanent-change detector card. As an alternative or additional measure, some embodiments use a shutter 320 that is kept closed until detector card 311 is in place and the MLS 122 is activated, such that shutter 320 limits the duration of exposure or the number of pulses that are recorded on detector 311. Conversely, if light transmitted through a standard tissue phantom would affect too few layers of detector 311, the modified tissue phantom 341 in system 300 would be lightened and/or thinned (thus increasing the transmitted power and energy) in order that the desired range of stimulation intensities would activate the available range of colors on the permanent-change detector card. As an alternative or additional measure, some embodiments use a shutter 320 that is kept closed until detector card 311 is in place and the MLS 122 is activated, and then shutter 320 is kept open for a longer time or MLS 122 is activated to emit enough pulses such that the duration or the number of pulses that are recorded are sufficient to affect the desired range of layers on detector 311. In some embodiments, the tissue phantom 341 and the permanent-change detector paper 311 are attached to a single handle inserted and moved from a single side of enclosure 310 (e.g., the top side) such that one spot is exposed and recorded for each of a plurality of different tissue-phantom thicknesses 351, 352, 353, 354, and/or 355, and/or with no tissue phantom (i.e., with the laser beam shined directly onto the permanent-change detector paper 311), thus recording the light intensities for each of a plurality of different tissue depths, and/or conversely, the tissue depth reached by a particular light intensity. In some embodiments, the permanent-change detector card shows markings for the thickness of the tissue phantom 341 at that location and/or has grid lines to allow the user to measure the size or shape of the transmitted light beam.

In some embodiments, a plurality of different detectors 311 are mounted on handles 312 and inserted into aperture 105, such that either a real-time-viewable up-conversion disc, such as a VIEW-IT® disc, or a permanent-change card (such as ZAP-IT® paper) may be interchangeably installed in system 300 with one or more different tissue phantoms 341, in order to interactively view and/or permanently record the shape, size and intensity of the nerve-stimulation laser beam (i.e., wherein a particular brightness of the up-conversion spot or the ZAP-IT spot, correlated with a given tissue-phantom thickness, indicates the tissue depth to which the stimulation-effective portion of the laser beam reaches).

In some embodiments, the detector 311 includes a strip of material that permanently discolors or changes to expose lower layers of material having contrasting color or brightness when exposed to a high enough irradiance (e.g., a burn strip).

In some embodiments, the detector 311 includes a laser-sensitive ceramic material such as VIEW-IT®. (such as are available from Kentek Corporation, 1 Elm St., Pittsfield, N.H. 03263, United States), which is a high-efficiency, laser-sensitive ceramic disc that provides a convenient method of viewing beam shape, mode structure and beam alignment when held in the path of a laser beam, and provides continuous viewing of the laser beam in action. VIEW-IT® provides an unlimited period of viewing for both pulsed and continuous wave lasers. Beam quality and mode structures can be observed in real time using their white ceramic disc with strong nonlinear (up-conversion) on a base of unique ion combination. This nonlinear optical process doubles the initial laser beam frequency. For example, if an initiated wavelength of 1064 nm (1.06 g) strikes the VIEW-IT® disc, it will be observed as green light.

In some embodiments, the detector 311 includes a laser-sensitive cards (such as Model F-IRC1, F-IRC2, and F-IRC-4 cards, which are available from Newport Corporation, 1791 Deere Avenue, Irvine, Calif. 92606. These allow the present invention to locate and analyze light beams in the 0.7-1.7 mm wavelength range with these pocket sized, low-cost IR detectors. These cards contain a special sensor area that emits clearly visible light when illuminated by near infra-red (NIR) and infra-red (IR) sources. Model F-IRC1, F-IRC2, and F-IRC-4 are credit card-size cards containing a 2 in. (50 mm) square sensor area. Model F-IRC2-F is also a smaller card containing a 0.5 in. (12.5 mm) square sensor area, and is used primarily with optical fiber outputs. The F-UVC1 is an Ultraviolet sensor card with 2 in. (50 mm) square sensor area for locating and analyzing light beams in the 0.24-0.60 mm wavelength range. The IR sensor cards are encapsulated between durable clear plastic layers. The UV sensor card has the protective polyester coating removed from the front of the sensor.)

In some embodiments, detector 311 is made of one or more strips that reversibly change color at different irradiances. In some embodiments, detector 311 includes a liquid-crystal detector (such as are available from B&H Liquid Crystal Resources Ltd, Riverside Buildings, Dock Road, Connahs Buildings, Dock Road, Connahs Quay, Deeside, Flintshire, CH5 4DS, Great Britain, which shows both the beam diameter and irradiance gradients within the beam). In other embodiments, the detector 311 performs temperature measurement using liquid crystals such as described in U.S. Pat. No. 6,585,411 that issued to Hammarth, et al. on Jul. 1, 2003, U.S. Pat. No. 4,064,872 (Caplan), issued Dec. 27, 1977; U.S. Pat. No. 6,257,759 (Witonsky, et al.), issued Jul. 10, 2001; U.S. Pat. No. 6,294,109 (Ratna, et al.); and U.S. Pat. No. 6,284,078 (Witonsky, et al.), issued Sep. 4, 2001, each of which is incorporated herein by reference.

In some embodiments, detector 311 includes a material or surface having a reversible thermochromic pigment (such as described in U.S. Pat. No. 5,480,482 that issued to Novinson on Jan. 2, 1996 entitled "Reversible thermochromic pigments", which is incorporated herein by reference), used to provide a reusable indicator of beam intensity and extent.

In some embodiments, the detector 311 includes one or more strips that irreversibly change color at different irradiances (such as Tempilabel and Thermax, available from Tempie, Inc., 2901 Hamilton Blvd, South Plainfield, N.J. 07080). These allow the present invention to monitor and verify temperature specific operations such as spot size and intensity. In some embodiments, they feature adhesive backing allowing them to be affixed to any surface quickly and easily. When desired temperature is reached the dot in the middle changes to black and remains that way indicating that the desired temperature has been reached. Accurate to +/−2% of the Fahrenheit rating, Tempilabel and Thermax brands are both available in either the multiple temperature range configuration or single temperature design.

In some embodiments, detector 311 includes a material or surface having a thermochromic ink (such as described in U.S. Pat. No. 6,669,765 that issued to Senga, et al. on Dec. 30, 2003 entitled "Thermochromic dry offset ink, and printed article produced using the same", which is incorporated herein by reference). In some embodiments, detector 311 includes a material or surface having thermochromic fibers or fabric (such as described in U.S. Pat. No. 6,444,313 that issued to Ono, et al. on Sep. 3, 2002 entitled "Thermochromic acrylic synthetic fiber, its processed article, and process for producing thermochromic acrylic synthetic fiber", or U.S. Pat. No. 4,681,791 that issued to Shibahashi, et al. on Jul. 21, 1987 titled "Thermochromic textile material", which are incorporated herein by reference).

In some embodiments, detector 311 includes a high-resolution infrared thermography system with a near-infrared camera (such as described in U.S. Pat. No. 7,040,805 that issued to Ou, et al. on May 9, 2006 titled "Method of infrared thermography", which is incorporated herein by reference).

FIG. 3 is also a schematic of a TPDM 300 that can also be used in a dynamic mode (rather than creating a permanent record on a one-time-use card as described above for FIG. 3) to display the IR output from a MLS 322 as visible light. In contrast to the invention described above for TPDM 200, which optically and electrically processes the light created by MLS 322, TPDM 300 directly converts this light into a visible light source or a permanent color change via an IR-to-visible conversion screen (IRVCS) 311. In some embodiments, the visible light pattern created by the IRVCS 311 can be observed from the exterior of the TPDM 300 because one side of the IRVCS 311 faces the interior of the TPDM 300 and receives the IR light and the other side of the IRVCS 311 faces the exterior of the TPDM 300 and emits the visible light. As with the TPDM 200 and TPDM 100, the TPDM 300 also contains a tissue phantom 342, which is connected to a handle 342 for easy changing of simulated tissue depths, or for removal.

In some embodiments, the TPDM of FIG. 1, FIG. 2, or FIG. 3 comes with wipes and solution for cleaning the windows and probe ends. In some embodiments, wipes and solution are not needed because the TPDM is disposable.

In some embodiments of the present invention, a method is described that includes providing a light from an optical source, optically processing (e.g. transmitting, reflecting, scattering, absorbing, and emitting) the light using a tissue phantom, detecting the transmitted light (which, in some embodiments, is a simulated stimulation pattern formed by the light), electrically processing the detector output, and displaying a numeric readout that corresponds to an optical characterization associated with the light.

In some embodiments of the present invention, an apparatus is described that includes a light from an optical source, a tissue phantom, an optical processing unit, an electrical processing unit, and a display for displaying a numeric readout that corresponds to an optical characterization associated with the light.

In some embodiments the present invention includes an apparatus comprising means for providing light from an optical source, means for simulating an organic tissue, means for optically processing the light using a simulated organic tissue, means for detecting the transmitted light, means for electrically processing the transmitted light, and means for displaying a numeric or graphical readout that corresponds to an optical characterization of the light.

In some embodiments, the present invention provides a method that includes receiving light from an optical source, providing a tissue phantom, transmitting at least a portion of the light through the tissue phantom, detecting the transmitted light and generating an electrical signal that characterizes the light transmitted through the tissue phantom, electrically processing the electrical signal, and displaying a representation of the electrically processed characterization associated with the light.

In some embodiments, the providing of the tissue phantom includes providing a plurality of areas on the tissue phantom including a first area and a second area, and wherein within the first area, the tissue phantom has a substantially constant first thickness, and within the second area, the tissue phantom has a substantially constant second thickness, and wherein the second thickness is different than the first thickness.

In some embodiments, the providing of the tissue phantom includes providing an area on the tissue phantom having a continuously varying thickness.

In some embodiments, the providing of the tissue phantom includes providing a plurality of areas on the tissue phantom including a first area and a second area, and wherein within the first area, the tissue phantom has a material representing a first tissue type, and within the second area, the tissue phantom has a material representing a second tissue type, and wherein the second tissue type is different than the first tissue type.

In some embodiments, the transmitted light corresponds to a pattern that simulates a pattern that would occur if the light were used to stimulate an animal tissue.

In some embodiments, the displaying includes displaying a plurality of different characteristics of the transmitted light.

In some embodiments, the displaying includes displaying a plurality of different characteristics of the transmitted light along each of a plurality of different transverse axes.

In some embodiments, the displaying includes displaying a numeric representation of an intensity of the transmitted light.

In some embodiments, the displaying includes displaying an iso-intensity map of the transmitted light.

In some embodiments, the displaying includes displaying a graph of light intensity along a cross-section of the transmitted light.

In some embodiments, the present invention provides an apparatus (e.g., system 100 of FIG. 1A, or system 200 of FIG. 2) that includes a first port configured to receive light from an optical source, a tissue phantom positioned such that at least a portion of the light passes through the tissue phantom, an optical detector operatively coupled to receive a portion of the light that passed through the tissue phantom and operable to generate a signal representing a characteristic of the received light, an electrical processing unit operatively coupled to receive the signal from the optical detector and operable to generate displayable information based on the signal, and a display operatively coupled to the electrical processing unit and configured to display the displayable information.

Some embodiments further include a second port configured to allow movement of the tissue phantom in order that different areas of the tissue phantom are successively placed between the received light and the detector.

Some embodiments further include a shutter configured to allow light to be detected only during a predetermined period of time.

Some embodiments further include a neutral density filter configured to reduce the intensity of light falling on the detector by a predetermined amount.

Some embodiments further include a lens or other focusing element (e.g., lens 147 of FIG. 1 or imaging optics 212 of FIG. 2) configured to form an image onto the detector of the transmitted light from the tissue phantom.

In some embodiments, the detector includes an infrared photocell (e.g., element 132 of FIG. 1).

In some embodiments, the detector includes a two-dimensional array of pixels, each pixel detecting an amount of light falling on a predetermined area (e.g., element 232 of FIG. 2).

In some embodiments, the tissue phantom (e.g., tissue phantom 151 of FIG. 1D) includes a first area and a second area, and wherein within the first area, the tissue phantom has a substantially constant first thickness, and within the second area, the tissue phantom has a substantially constant second thickness, and wherein the second thickness is different than the first thickness.

In some embodiments, the tissue phantom (e.g., tissue phantom 150 of FIG. 1C) includes an area having a continuously varying thickness.

In some embodiments, the tissue phantom (e.g., tissue phantom 151 of FIG. 1D) includes a first area and a second area, and wherein within the first area, the tissue phantom has a material representing a first tissue type, and within the second area, the tissue phantom has a material representing a second tissue type, and wherein the second tissue type is different than the first tissue type.

Some embodiments further include a handle (e.g., element 142 of FIG. 1A, element 243 of FIG. 2, or element 342 of FIG. 3) connected to the tissue phantom so that the tissue phantom can easily be inserted and removed from the path of the light being received from the optical source.

In some embodiments, the displayable information includes a numeric representation of an intensity of the transmitted light (e.g., element 134 of FIG. 1A).

In some embodiments, the displayable information includes an iso-intensity map of the transmitted light (e.g., element 251 of FIG. 2).

In some embodiments, the displayable information includes a graph of light intensity along a cross-section of the transmitted light (e.g., element 252 of FIG. 2).

In some embodiments, the present invention provides means for receiving light from an optical source, means for simulating the optical properties of organic tissue, means for transmitting at least a portion of the received light through the means for simulating the organic tissue, and means for displaying information about the light transmitted through the means for simulating organic tissue.

In some embodiments, the means for simulating the optical properties of organic tissue includes a means for representing organic tissue with a plurality of substantially constant and discrete thicknesses.

In some embodiments, the means for simulating the optical properties of organic tissue includes a means for representing organic tissue with a continuously varying thickness.

In some embodiments, the means for simulating the optical properties of organic tissue includes a means for representing a plurality of different organic tissue types on one device.

In some embodiments, the means for visibly displaying information about the transmitted light includes a means for numerically displaying a value of an intensity of the transmitted light.

In some embodiments, the means for visibly displaying information about the transmitted light includes a means for displaying an intensity of the transmitted light using iso-intensity lines.

In some embodiments, the means for visibly displaying information about the transmitted light includes a means for graphically displaying an intensity of the transmitted light along a cross-section of the transmitted light.

In some embodiments, the present invention provides an apparatus (e.g., tissue phantom 149 of FIG. 1B, tissue phantom 150 of FIG. 1C, tissue phantom 151 of FIG. 1D, system 100 of FIG. 1A, system 200 of FIG. 2, or system 300 of FIG. 3) that includes a tissue phantom having a plurality of side-by-side areas each representing different tissue characteristics related to light transmission through organic tissue.

In some embodiments, the tissue phantom (e.g., tissue phantom 151 of FIG. 1D) includes a first area and a second area, and wherein the tissue phantom within the first area has a substantially constant first thickness, and the tissue phantom within the second area has a substantially constant second thickness, and wherein the second thickness is different than the first thickness.

In some embodiments, the tissue phantom (e.g., tissue phantom 150 of FIG. 1C) includes an area having a continuously varying thickness.

In some embodiments, the tissue phantom (e.g., tissue phantom 151 of FIG. 1D) includes a first area and a second area, and wherein within the first area, the tissue phantom has a material representing a first tissue type, and within the second area, the tissue phantom has a material representing a second tissue type, and wherein the second tissue type is different than the first tissue type.

In some embodiments, the tissue phantom includes a first area and a second area, and wherein the tissue phantom within the first area has a material representing a first tissue type stacked on a material representing a second tissue type, and wherein the second tissue type is different than the first tissue type, and wherein the tissue phantom within the first area has a material representing a third tissue type.

Some embodiments further include a handle (e.g., element 142 of FIG. 1A, element 243 of FIG. 2, or element 342 of FIG. 3) connected to the tissue phantom so that the tissue phantom can easily be inserted and removed from the path of the transmitted light.

Some embodiments further include an optical detector operatively coupled to receive a portion of light that passed through the tissue phantom and operable to display a representation of a characteristic of the received light. In some embodiments, the optical detector is configured to be separated from the tissue phantom after exposure to the light to provide a lasting representation of a characteristic of transmitted light.

Some embodiments further include an enclosure configured to hold the tissue phantom and a removable display card held in a fixed relationship to the tissue phantom by the enclosure, wherein the enclosure is configured to receive light from a medical light source at a predetermined distance from the tissue phantom and wherein the enclosure is configured to allow the removable display card to be removed after exposure to the light to provide a lasting representation of a characteristic of transmitted light.

In some embodiments, the present invention provides an apparatus that includes a first port configured to receive light from an optical source; a tissue phantom positioned such that at least a portion of the light passes through the tissue phantom; and an optical detector and display operatively coupled to receive a portion of the light that passed through the tissue phantom and operable to generate a visible representation of a characteristic of the received light. In some such embodiments, the detector and display are a unitary non-electronic laser-beam display unit, such as a frequency-doubling card (e.g., a cardboard substrate with a non-linear up-conversion material) that up-converts and displays infrared light (e.g., 1064 nm laser signal) as 532 nm visible green light, or such as a liquid-crystal thermographic display (irreversibly or reversibly changed by the laser beam, depending on the embodiment).

Some embodiments further include a tissue-phantom positioner configured to position one or more of a plurality of portions of the tissue-phantom between the first port and the optical detector, wherein the tissue phantom further comprises a first area and a second area, and wherein within the first area, the tissue phantom has a substantially constant first thickness, and within the second area, the tissue phantom has a substantially constant second thickness, and wherein the second thickness is different than the first thickness.

Some embodiments further include a tissue-phantom positioner configured to position one or more of a plurality of portions of the tissue-phantom between the first port and the optical detector, wherein the tissue phantom further comprises an area having a continuously varying thickness.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for characterizing an optical source comprising:
   obtaining light from the optical source;
   providing a tissue phantom having a light-input face and a light-output face opposite the light-input face, wherein the light-input face includes a first planar area;
   at a first time, transmitting a portion of the light through a first volume of the tissue phantom that is located between the first planar area of the light-input face and the light-output face such that the light enters the first volume of the tissue phantom through the first planar area of the light-input face and the portion of the light that transmits through the first volume of the tissue phantom exits the first volume of the tissue phantom through a second planar area of the light-output face that is opposite the first planar area of the light-input face;
   at the first time, receiving the transmitted light from the second planar area of the light-output face that is opposite the first planar area of the light-input face as a characterization of the portion of the light transmitted through the first volume of the tissue phantom, wherein the receiving of the transmitted light further comprises generating an electrical signal that characterizes the portion of the light transmitted through the first volume of the tissue phantom and electrically processing the electrical signal; and displaying a representation of the characterization associated with the portion of the light transmitted through the first volume of the tissue phantom, wherein the displaying includes displaying a representation of the electrically processed characterization associated with the portion of the light transmitted through the first volume of the tissue phantom, wherein the displaying includes displaying an iso-intensity map of the transmitted light, wherein the first area of the light-input face of the first volume on the tissue phantom is not parallel to the light-output face of the first volume opposite the first area, such that there is a continuously varying thickness between the first area of the light-input face and the light-output face opposite the first area, and wherein the thickness varies at a constant rate.

2. The method of claim 1, wherein the providing of the tissue phantom includes providing a plurality of side-by-side volumes of the tissue phantom including the first volume and a second volume, wherein the first volume of the tissue phantom has a first thickness between the first area of the light-input face and the light-output face opposite the first area, wherein the method further includes at a second time, transmitting a portion of the light through a second volume of the tissue phantom that is located between a second area of the light-input face and the light-output face such that the light enters the second volume of the tissue phantom through the second area of the light-input face and the portion of the light that transmits through the second volume of the tissue phantom exits the second volume of the tissue phantom through an area of the light-output face that is opposite the second area of the light-input face; and at the second time, receiving the transmitted light from the area of the light-output face that is opposite the second area of the light-input face as a characterization of the portion of the light transmitted through the second volume of the tissue phantom, wherein a plane of the second area of the light-input face is parallel to a plane of the light-output face that is opposite the second area of the light-input face, and wherein the second area of the tissue phantom has a second thickness between the light-input face of the second area and the opposite light-output face of the second area, and wherein the second thickness is different than the first thickness.

3. The method of claim 1, wherein the providing of the tissue phantom includes providing a plurality of side-by-side volumes of the tissue phantom including the first volume and a second volume, wherein the first volume of the tissue phantom has a material between the first area of the light-input face and the light-output face opposite the first area representing a first tissue type, wherein the method further includes at a second time, transmitting a portion of the light through a second volume of the tissue phantom that is located between a second area of the light-input face and the light-output face such that the light enters the second volume of the tissue phantom through the second area of the light-input face and the portion of the light that transmits through the second volume of the tissue phantom exits the second volume of the tissue phantom through an area of the light-output face that is opposite the second area of the light-input face; and at the second time, receiving the transmitted light from the area of the light-output face that is opposite the second area of the light-input face as a characterization of the portion of the light transmitted through the second volume of the tissue phantom, wherein a plane of the second area of the light-input face is parallel to a plane of the light-output face opposite the second area, wherein the second volume of the tissue phantom has a material between the light-input face of the second volume and the opposite light-output face of the second volume representing a second tissue type, and wherein the second tissue type is different than the first tissue type.

4. The method of claim 1, wherein the transmitted light corresponds to a pattern that simulates a pattern that would occur if the light were used to stimulate an animal tissue.

5. The method of claim 1, wherein the displaying includes displaying a plurality of different characteristics of the transmitted light.

6. The method of claim 1, wherein the displaying includes displaying a plurality of different characteristics of the transmitted light along each of a plurality of different transverse axes.

7. The method of claim 1, wherein the displaying includes displaying a numeric representation of an intensity of the transmitted light.

8. An apparatus for characterizing an optical source comprising:

a first port configured to receive light from the optical source;

a tissue phantom having a light-input face and a light-output face opposite the light input face, wherein the light-input face includes a first planar area, wherein the tissue phantom is positioned such that, at a first time, a portion of the light passes through a first volume of the tissue phantom such that the light enters the first volume of the tissue phantom through the first planar area of the light-input face and the portion of the light that transmits through the first volume of the tissue phantom exits the first volume of the tissue phantom through a second planar area of the light-output face that is opposite the first planar area of the light-input face;

an optical detector operatively coupled to receive the portion of the light that passed through the first volume of the tissue phantom at a first time, and operable to generate a signal representing a characteristic of the light received by the optical detector;

an electrical processing unit operatively coupled to receive the signal from the optical detector and operable to generate displayable information based on the signal; and a display operatively coupled to the electrical processing unit and configured to display the displayable information, wherein the displayable information further comprises an iso-intensity map of the light received by the optical detector, wherein the first area of the light-input face of the first volume of the tissue phantom is not parallel to the light-output face of the first volume opposite the first area, such that there is a continuously varying thickness between the first area of the light-input face and the light-output face opposite the first area, wherein the thickness varies at a constant rate.

9. The apparatus of claim 8, wherein the light-input face of the tissue phantom further comprises a plurality of side-by-side planar areas including the first planar area and a second planar area, wherein the first volume of the tissue phantom has a first thickness between the first area of the light-input face and the light-output face opposite the first area, wherein a plane of the second planar area is parallel to a plane of the light-output face opposite the second area of the light-input face, wherein a second volume of the tissue phantom has a second thickness between the second area of the light-input face and the light-output face opposite the second planar area, and wherein the second thickness is different than the first thickness.

10. The apparatus of claim 8, wherein the tissue phantom further comprises a plurality of side-by-side volumes including the first volume and a second volume, wherein the first volume of the tissue phantom has a material between the first area of the light-input face and the light-output face opposite the first area that represents a first tissue type, wherein a plane of a light-input face of the second area is parallel to a plane of a light-output face of the second area that is opposite the light-input face of the second volume, wherein the second volume of the tissue phantom has a material between the second area of the light-input face of the second volume and the light-output face opposite the second area that represents a second tissue type, and wherein the second tissue type is different than the first tissue type.

11. The apparatus of claim 8, wherein the displayable information further comprises a numeric representation of an intensity of the light received by the optical detector.

12. The apparatus of claim 8, wherein the displayable information further comprises a graph of light intensity along a cross-section of the light received by the optical detector.

* * * * *